United States Patent [19]

Ruf

[11] Patent Number: 4,562,588
[45] Date of Patent: Dec. 31, 1985

[54] POSITIONING DEVICE FOR AN EXTENSION AND REPOSITIONING APPARATUS

[76] Inventor: Hermann Ruf, Pfutzenstrasse 58, 6103 Griesheim, Fed. Rep. of Germany

[21] Appl. No.: 441,042

[22] Filed: Nov. 12, 1982

[30] Foreign Application Priority Data

Nov. 20, 1981 [DE] Fed. Rep. of Germany ... 8133813[U]

[51] Int. Cl.$^4$ .............................................. A61B 17/18
[52] U.S. Cl. .................................... 378/208; 269/328; 128/133; 378/180
[58] Field of Search ............... 378/208, 180, 209, 177, 378/18, 20; 248/118, 315; 128/653, 303 B, 133; 269/328; 5/443

[56] References Cited

U.S. PATENT DOCUMENTS

| | | | |
|---|---|---|---|
| 2,757,058 | 3/1956 | Broesel | 269/328 |
| 3,027,895 | 4/1962 | Williams | 128/133 |
| 3,913,561 | 10/1975 | Maeda | 378/164 |
| 4,053,781 | 10/1977 | Hounsfield | 378/180 |
| 4,187,423 | 2/1978 | Ehrhardt | 378/164 |

FOREIGN PATENT DOCUMENTS 2602228  8/1977  Fed. Rep. of Germany ...... 378/208

Primary Examiner—Craig E. Church
Assistant Examiner—Charles F. Wieland
Attorney, Agent, or Firm—Andrus, Sceales, Starke & Sawall

[57] ABSTRACT

A positioning device for use with an extension and repositioning apparatus for the orientation of an extremity comprises a support cradle for the extremity and a connection element. The support cradle is formed of a lower post fastened to the extension and repositioning apparatus. The support cradle is further formed of a laterally projecting support arm and a raised mounting arm essentially parallel to the post. The connection element is couplable to the support cradle by releasable pin connections to secure a limb. The support cradle and connection element may be formed of sterilizable, X-ray transparent plastic material.

15 Claims, 8 Drawing Figures

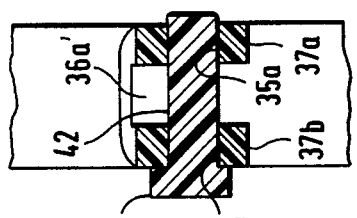
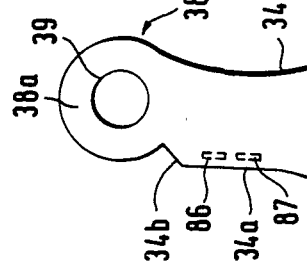
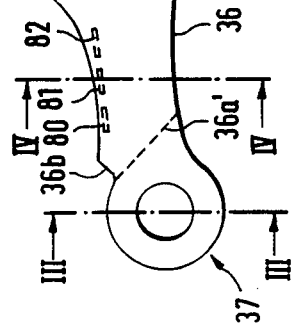
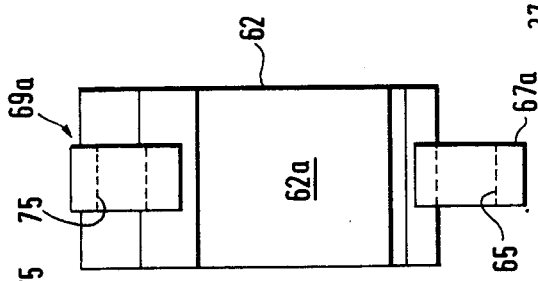
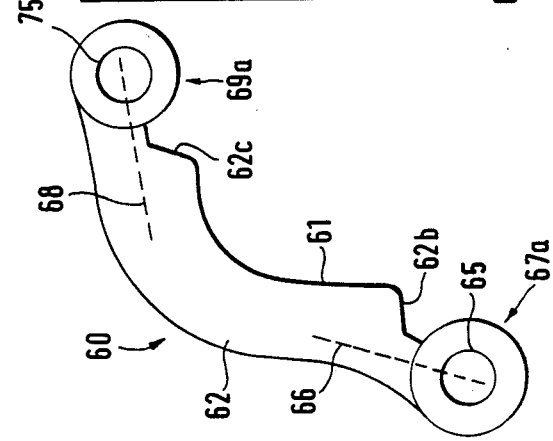

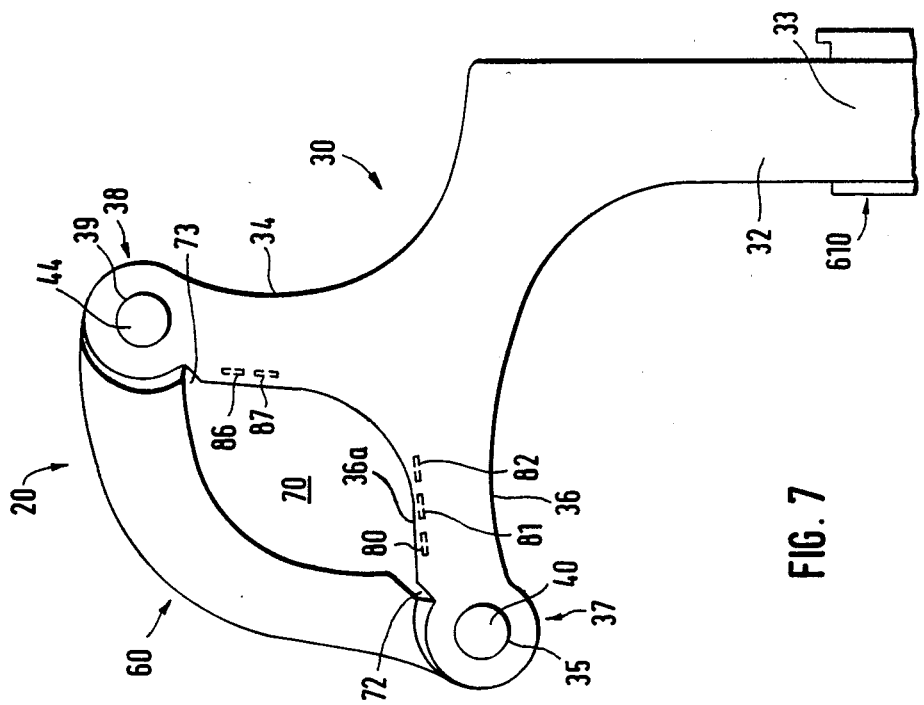
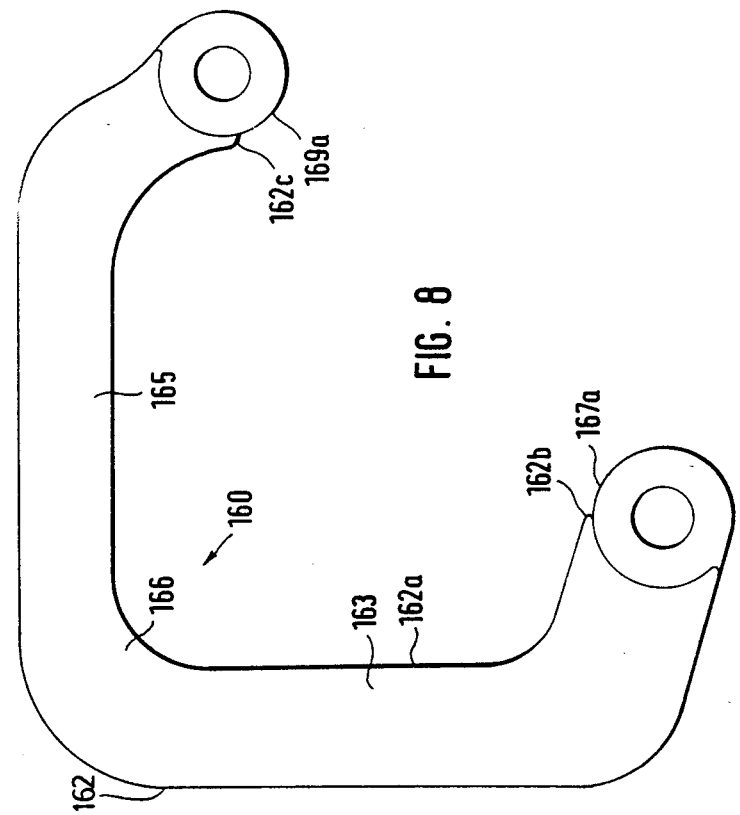
FIG. 7
FIG. 8

POSITIONING DEVICE FOR AN EXTENSION AND REPOSITIONING APPARATUS

The invention relates to a positioning device for use with an extension and repositioning apparatus for the orientation of an extremity. The device comprises a support cradle for the extremity formed of a sterilizable, X-ray transparent material and a connection element. The connection element provides a coupling member on each of its two free ends. The support cradle is formed of a lower post fastened in a retainer for the attachment of the support cradle in a support of the apparatus. The support cradle is further formed of a laterally projecting support arm and a raised mounting arm essentially parallel to the post, whereby a complementary coupling element is formed on the free end of the mounting arm and on the free end of the support arm.

In DE-OS No. 2,602,228, an extension apparatus and repositioning apparatus is described for the orientation and treatment of broken bones, in particular for the closed pinning of bones with the use of modern X-ray equipment. In the head of this apparatus a support cradle formed out of a sterilizable X-ray transparent plastic material is fastened. The basic principle of this apparatus can be traced back to the extension table developed by Dr. R. Wittmoser in 1943.

With the earlier embodiments of the extension table, wooden holding rings were used instead of the support cradle. These are however not sterilizable and are formed out of a larger number of hand finished individual parts. The sterilizable support cradle according to the mentioned Offenlegungsschrift can be closed through employment of adjustable plastic straps, that are laid about the extremity and fastened on the support arm and the mounting arm. The use of the plastic straps have the disadvantage that they can be sterilized only with great difficulty. Also they easily cut into the soft parts of the extremity and are thus uncomfortable for the patient. Further, the plastic straps are readjusted only with difficulty to a changed circumference of another section of the extremity lying on the support cradle.

The object of the present invention is to provide a positioning device of the initially described type that is fully sterilizable and so formed that it does not cut into soft parts and can fit easily different thicknesses of the extremity parts.

The positioning device according to the invention is characterized in that the connection element is a rigid half ring formed out of a sterilizable, X-ray transparent, plastic that completes the ring section formed out of the support arm and the mounting arm to a closed ring and that the coupling parts formed on the free ends of the half ring and the complementary coupling parts are formed as detachable pin connections. Thus can each extremity portion be held in the support cradle without discomfort for the particular patient selected. The pin connection makes possible an easy exchange of a half ring for a greater or lesser convexly bent half ring exactly fitting the circumference of the extremity part to be oriented, so that the head adjustment need not be changed.

If the half ring is bent convexly outward in such a manner that the direction of its free ends subtend an acute angle, a very large extremity part can be accommodated with the positioning device. For thin extremity parts, a half ring flat bent in such a manner that the direction of its free ends subtend an obtuse angle is recommended.

The accessibility for the recording camera and the X-ray equipment to the positioned extremity part is enhanced in a further configuration of the invention in that the mounting arm is formed on the post displaced relative to the post in the direction of the support arm, so that the support is then located outside of the exposure region of the X-ray equipment.

As plastic material pure polyethylene is recommend that possesses outstanding X-ray transparency and sterilizability.

In order to produce as wide as possible support surfaces for the extremity, the transverse section of the support arm is preferably a rectangle with greatly rounded corners. The large rounding prevents irritating pressing in of the support arm in the soft tissue portions.

The recognition of the orienting position on the X-ray film is facilitated through reference marks that are provided in a further form of the invention through metal pieces embedded in the support arm as well as also in the mounting arm. The support arm can be differentiated from the mounting arm on the X-ray image through the different number of reference marks when, in a further configuration of the invention, a differing number of metal pieces, preferably formed out of copper strips, are embedded in the support arm and the mounting arm. The metal pieces can also have a different size in the support arm, for example wider or longer, than the metal pieces in the mounting arm.

The interchangeability of the half rings on the support cradle is simplified in a preferred manner in that the coupling parts on the half ring are formed as loops with eyes, the inner diameter of which is essentially equal to the outer diameter of a pin that projects out of the complementary coupling part. Also, each complementary coupling part can be formed out of a loop with an eye on the support arm and on the mounting arm, so that a separate pin is insertable through the eye of the coupling part and the complementary coupling part. The loops of the coupling parts can be inserted between each of a loop pair on the complementary coupling part until alignment of the eyes occurs.

The adherence of the soft tissue portions in the region of the coupling parts and the complementary coupling parts is preferably eliminated with certainty in that the support arm, the mounting arm, and the half ring are cut away next to the eyes so no oppositely lying edges are provided.

The invention is further described in detail with the aid of exemplary embodiments disclosed in the attached drawings. The drawings show:

FIG. 1 a schematic perspective view of an extension and repositioning apparatus with attached positioning device;

FIG. 2 is a schematic side view of a support cradle of the positioning device;

FIG. 3 is a schematic view of a section through the support cradle according to FIG. 2 along the line III—III;

FIG. 4 is a schematic view of a section through the support cradle according to FIG. 2 along the line IV—IV;

FIG. 5 is a schematic side view of a half ring for the support cradle according to FIG. 2;

FIG. 6 is a schematic front view of the half ring according to FIG. 5;

FIG. 7 is a schematic side view of the support cradle according to FIG. 2 with attached half ring according to FIG. 5; and FIG. 8 is a schematic side view of another exemplary form of a half ring.

Figure 1:
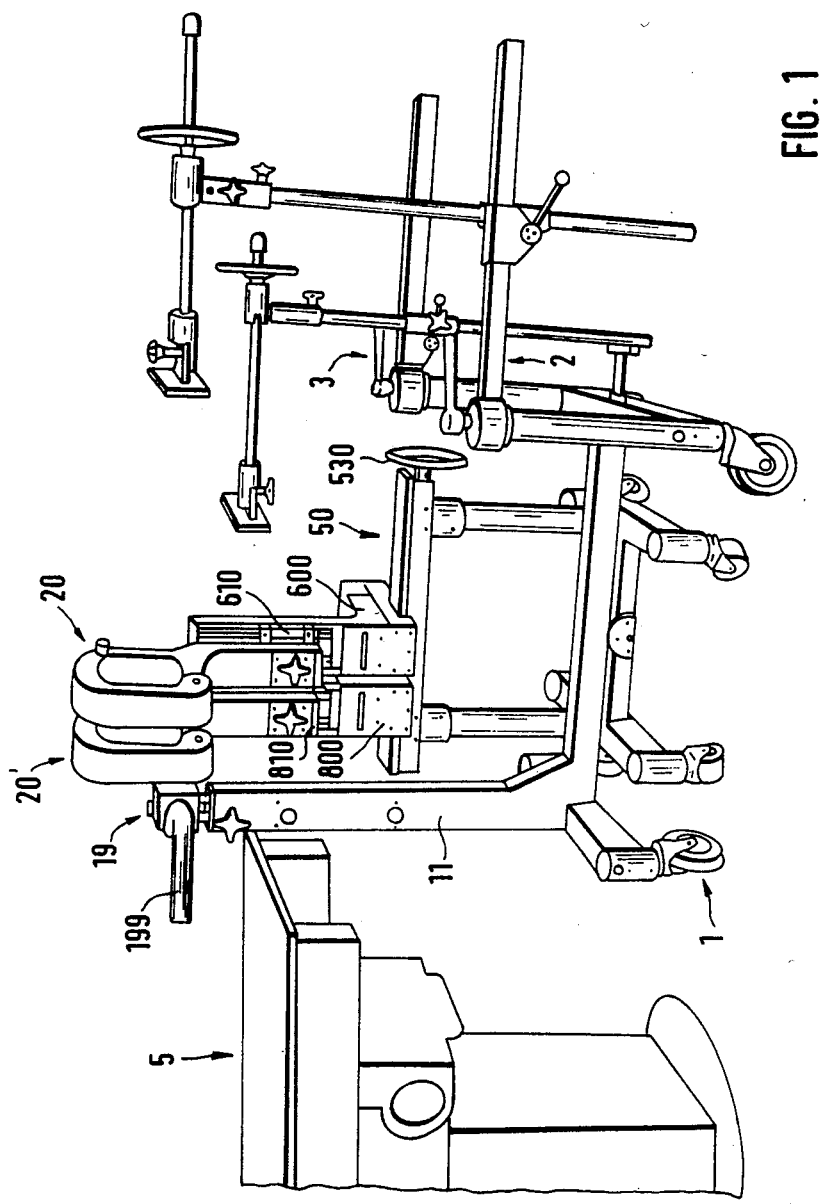

The movable extension and repositioning apparatus according to FIG. 1 arranged in front of the front face of an operating table 5 is formed out of an extension table indicated in its entirety with 1 and a repositioning mount 50. Extension table 1 and repositioning mount 50 make possible, together with the positioning device, 20a according to the invention, a definitive positioning and orientation of a leg of a patient lying on the operating table. The extension table has, for its part, an upright on the upper end of which is provided a rest appropriate for the upper thigh. On the oppositely lying end of the extension table 1 two laterally displaced extension links 2, 3 rotatable about 360° are fastened on the table frame. Each of the links carries a counterplate for the securing of a foot of the patient.

Between the upright 11 and the extension links 2, 3 the repositioning mount 50 is inserted, on the table of which two supports 600, 800 are displaceable separately or together in the longitudinal direction of the operating table 5 by means of a hand crank 530. Each support possesses a horizontal sliding carriage and a vertical sliding carriage, whereby on the vertical sliding carriage 610 the positioning device 20 is detachably mounted. On the vertical sliding carriage 810 of the support 800 a further positioning device 20' is fastened. The positioning devices 20 and 20' are similarly constructed so that for the present explanation only the positioning device 20 is described below in detail. Each of the positioning devices 20, 20' can be individually traversed in three normal spatial directions by means of the handwheel 530 as well as by means of the horizontal sliding carriage and of the vertical sliding carriage.

The positioning device 20 (FIG. 7) is formed essentially of a support cradle 30 and a half ring 60. The support cradle 30 has a lower post 32 which is connected at its lower section 33 with the vertical sliding carriage 610. The upper end of the post 32 branches in a vertical mounting arm 34 laterally displaced from opposite the post 32 and extending essentially parallel to the post, as well as in a horizontal outwardly projecting support arm 36. The upper end of the mounting arm 34 carries a loop-like formed hinge head 38 with a middle eye 39. The outer free end of the support arm 36 is formed for a similar hinge head 37, that surrounds an eye 35.

As one can appreciate from the FIG. 3, the hinge head 37 is formed of two parallel spaced discs 37a and 37b, the aligned holes of which form each of the eyes 35a and 35b. The forward front faces 36a' of the support arm 36 run downwardly in the rearward direction (indicated dotted in FIG. 2), in order to permit a free space between the disc formed coupling element 67a of a half ring 60 inserted between the two discs 37a and 37b. A pin 40 can be inserted with its shaft 42 in the eyes 35a and 35b of the hinge head 37 forming a complementary coupling part as well as through the eye 65 of the coupling element 67a, so that in this manner the half ring is rotatably fastened on an end with the hinge head 37 of the support arm 36. Through extraction of the pin shaft 42 from the eyes 35a, 65 and 35b this connection can easily be released.

The hinge head 38 on the upper end of the mounting arm 34 is formed essentially in the same manner as the hinge head 37 of the support arm 36. A further pin 44 (FIG. 7) can be inserted with its shaft through the eye 39 and makes possible, in coaction with an eye 75 on the free end of the half ring 60 lying opposite to the eye 65, a detachable pin connection of the half ring 60 with the upper end of the mounting arm 34. With the illustration selected in FIG. 2 only the coupling disc 38a with the eye 39 is apparent, a parallel further coupling disc is formed at a distance behind the coupling disc 38a.

The main part 62 of the half ring 60 (FIGS. 5 and 6) has only a slightly convexly bent form, and possesses on each of its oppositely lying free ends a coupling element 67a and 69a. The coupling element 67a and the coupling element 69a are each a disc formed in the middle of the lateral extension of the main part 62 that is provided with concentric eyes 65 and 75, respectively. The thickness of the coupling elements 67a and 69a is slightly smaller than the spacing of the discs 37a and 37b, and the discs of the hinge head 38 forming the complementary coupling, so that after the insertion of the coupling elements 67a and 69a between the corresponding plates of the complementary coupling parts 37a and 37b, the respective eyes align. As one can appreciate particularly from FIG. 5, the half ring 60 is so slightly convex that the directions 66 and 68 of its free ends subtend an obtuse angle. The inner contour 61 of the main part 62 describes however approximately a 90° angle.

The half ring 60 is connected with the support cradle 30 in the manner shown in FIG. 7 so that when the pins 40 and 44 are inserted in the corresponding eyes, the support arm 36, the mounting arm 34 and the inner contour 61 of the half ring 60 surround an opening 70 and fix an extremity part located in the opening 70 against lateral displacement. The sensitive soft tissue parts find thus the wide support on the relatively broad supporting surface 36a of the support arm, that on the side shown in FIG. 4 is greatly rounded off. Thus the supporting surface 36a cannot cut into the soft tissue portions. Thus also the supporting surface 34a of the mounting arm 34 and the inner surface 62a of the main part 62 are sufficiently wide and laterally rounded off, that also through these parts no pressure points are permitted to develope in the stretched leg or arm.

It is to be further emphasized that the support surface 36a as well as the inner surface 62a and the support surface 34a at the transition to the coupling elements 67a and 69a as well as to the hinge heads 37 and 38 are bevelled through a respective slanting section 36b, 62b, 62c, and 34b, so that wide spaces 72, 73 remain with half ring 60 erected on the support cradle 30. These prevent, with the completion of the ring 20 through placing of the half ring 60 on the supporting cradle 30, soft tissue portions from being squeezed. The extension of the leg or arm in the opening 70 of the closed positioning device according to the invention thus occurs without injury to the condition of the patient and without disadvantageous effects on the sensitive soft tissue parts of the extended extremity part.

The support cradle 30, the half ring 60, as well as the pair of pins 40 and 44 are formed out of clean polyethylene that guarantees an outstanding sterilization ability and simultaneously the suitable X-ray transparency properties. In order that the positioning device otherwise not normally appearing in the picture can be located in the developed X-ray image, a plurality of copper strips 80, 81, 82 and 86, 87 are worked into the support arms 36 and into the installation arm 34 closely underneath the support surface 36a and the support surface 34a. The copper strips are viewable on the X-ray picture. In the disclosed exemplary embodiment, three copper strips, 80, 81, and 82 are cast next to each other in the support arm 36 and in the mounting arm 34 are, to differentiate, only two copper strips 86 and 87 embedded one above the other. The copper strips are impressed laterally appropriately in corresponding openings of the support arm 36 and of the mounting arm 34. The openings are subsequently imperviously closed so that no slits impairing the sterilizing properties remain.

A particular advantage of the invention resides in the fact that the support cradle 30 can be connected with a plurality of different half rings of differing convexity while avoiding the need to change the position of the leg or arm lying in the support cradle or the adjustment of the support cradle 30 relative to the repositioning mount 50. Thus the half ring 60 belongs to a group of, for example five different half rings of different bends, from which a half ring 160 with greater convexity is illustrated in FIG. 8. The half ring 160 carries on its two free ends plate formed coupling elements 167a and 169a that correspond in their form and arrangement relative to the main part 162 of the half ring 160 essentially to the coupling elements 67a and 69a. The main part 162 is formed out of two essentially straight sections 163 and 165, that in essence run at right angles to each other, and are connected with each other through a broad curvature 166, and on their ends transition through an angle to the corresponding coupling element 167a and 169a. The inner contour 162a as a result maintains an outwardly bent form, so that the opening, that is surrounded by the half ring 160 mounted on the support cradle 30 with the support arm 36 and the mounting arm 34, is essentially larger with respect to the opening 70. Thus an upper thigh can, for example, comfortably be placed in this larger opening. The inner surface of the half ring 160 is on the transition to the coupling elements 167a and 169a further smoothed through chamfer 162b, 162c in order to clearly preclude an adhesion of, for example, body hair upon the placing of the half ring 160 on the support cradle 30.

Additional, not disclosed, half rings can lie in their inner convexity between that of the half ring 60 and the half ring 160. However half rings with much greater convexity than the half ring 160 are also couplable without more to the support cradle. It is understood that all half rings can be manufactured out of clean polyethylene and are finished as a unitary element.

The invention is not limited in its details to the disclosed and described exemplary embodiments. The attached drawing as well as the claims are to be understood as completing or separating disclosures of the invention.

I claim:

1. A positioning device for orienting an extremity for taking X-rays of the extremity, said device being suitable for use in conjunction with extremity extension and repositioning apparatus, said device comprising a support cradle (30) and a connection element (60, 160), said support cradle and connection element being formed of a sterilizable, X-ray transparent material:

said support cradle (30) having a lower post (32) suitable for mounting said cradle on the extension and repositioning apparatus; said support cradle having a generally straight support arm (36) projecting horizontally outwardly from said post, the extremity being placed on top of said support arm when being oriented; said support cradle further having a generally straight mounting arm (34) adjacent said support arm extending vertically upward above said support arm and against which the extremity is placed when being oriented, said support arm and said mounting arm lying at an angle of approximately 90° to each other, said mounting arm being laterally displaced from said lower post (32) in the direction of projection of said support arm; each of said support arm and mounting arm having a free end, said free ends of said support and mounting arms containing means for coupling said support cradle to said connection element;

said connection element (60, 160) being formed as an elongated, inflexible, bent element to extend between said horizontal support arm and said vertical mounting arm, said connection element having coupling means on the ends thereof complementary to the coupling means of said support cradle for coupling said connection element to said support cradle; said support cradle and connection element, when coupled, forming a closed member suitable for surrounding the extremity placed on said support arm; and said coupling means on said support cradle and connection element being joined by removable pins for releasing one or both ends of said connection element from said support cradle.

2. The device according to claim 1 wherein said connection member (60) is so bent that the extensions of its ends (66, 68) subtend an obtuse angle (FIG. 5).

3. The device according to claim 1 wherein said connection element (160) is so formed that the extensions of its ends subtend an acute angle (FIG. 8).

4. The device according to claim 1 wherein said support cradle and connecting element are formed of polyethylene.

5. The device according to claim 1 wherein said support arm (36) possesses a broad, rounded support surface (36a) for supporting the extremity when placed on said support arm.

6. The device according to claim 5 wherein said support arm has a generally rectangular cross-sectional configuration, the corners of said rectangular configuration adjacent said support surface being rounded.

7. The device according to claim 1 wherein a plurality of adjacent metal pieces (80, 81, 82) are embedded in said support arm (36).

8. The device according to claim 1 wherein a plurality of adjacent metal pieces (86, 87) are embedded in said mounting arm (34).

9. The device according to claim 7 wherein a plurality of adjacent metal pieces (86, 87) are embedded in said mounting arm (34).

10. The device according to claim 9 wherein differing numbers of metal pieces are embedded in said support arm and in said mounting arm.

11. The device according to claim 7 wherein said metal pieces are formed of copper.

12. The device according to claim 8 wherein said metal pieces are formed of copper.

13. The device according to claim 9 wherein the metal pieces in said support arm (36) have a different size than the metal pieces in said mounting arm (34).

14. The device according to claim 1 wherein said coupling means on one of said support cradle or connecting element are formed as discs containing holes for said removable pins and wherein the coupling means on the other of said support cradle and connecting element are formed as pairs of loops straddling said discs and having eyes for receiving said removable pins.

15. The device according to claim 1 wherein said support arm, mounting arm, and connecting member have slanting surface (34b, 36b, 62b, 62c) adjacent said coupling means providing spaces (72, 73) that avoid pinching the extremity.

* * * * *